(12) United States Patent
Fujii et al.

(10) Patent No.: US 11,013,400 B2
(45) Date of Patent: May 25, 2021

(54) OPHTHALMIC APPARATUS

(71) Applicant: TOPCON CORPORATION, Tokyo (JP)

(72) Inventors: Kouta Fujii, Tokyo (JP); Makoto Saika, Tokyo (JP); Jun Sakai, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 246 days.

(21) Appl. No.: 16/139,195

(22) Filed: Sep. 24, 2018

(65) Prior Publication Data

US 2019/0090735 A1 Mar. 28, 2019

(30) Foreign Application Priority Data

Sep. 27, 2017 (JP) .............................. JP2017-186663

(51) Int. Cl.
*A61B 3/12* (2006.01)
*A61B 3/10* (2006.01)
*A61B 3/00* (2006.01)
*A61B 3/14* (2006.01)
*G01B 9/02* (2006.01)

(52) U.S. Cl.
CPC ............ *A61B 3/1005* (2013.01); *A61B 3/102* (2013.01); *A61B 3/12* (2013.01); *A61B 3/0008* (2013.01); *A61B 3/14* (2013.01); *G01B 9/0203* (2013.01)

(58) Field of Classification Search
CPC .......... A61B 3/1005; A61B 3/102; A61B 3/12
USPC ......................................... 351/205–206, 246
See application file for complete search history.

(56) References Cited

U.S. PATENT DOCUMENTS

| 2010/0302508 A1 | 12/2010 | Yamamoto et al. |
| 2012/0002164 A1* | 1/2012 | Yamamoto ............. A61B 3/102 351/206 |
| 2012/0189184 A1 | 7/2012 | Matsumoto et al. |

(Continued)

FOREIGN PATENT DOCUMENTS

| JP | H08-206081 A | 8/1996 |
| JP | H10-179517 A | 7/1998 |

(Continued)

OTHER PUBLICATIONS

EESR dated Feb. 27, 2019, issued in corresponding European Patent Application No. 18196590.6.

*Primary Examiner* — James R Greece
(74) *Attorney, Agent, or Firm* — Xsensus LLP

(57) ABSTRACT

An ophthalmic apparatus of an exemplary embodiment is capable of applying OCT to the fundus of a subject's eye, and includes an optical system, an optical scanner, an optical path length changing device, and a controller. The optical system splits light output front a light source into measurement light and reference light, projects the measurement light onto the fundus, generates interference light by superposing returning light of the measurement light from the subject's eye on the reference light, and detects the interference light. The optical scanner deflects the measurement light for scanning the fundus. The optical path length changing device changes at least one of an optical path length of the measurement light and an optical path length of the reference light. The controller controls the optical scanner based on at least the optical path length.

17 Claims, 7 Drawing Sheets

(56) References Cited

U.S. PATENT DOCUMENTS

| | | | | |
|---|---|---|---|---|
| 2014/0016095 A1* | 1/2014 | Takai | ..................... | A61B 3/102 |
| | | | | 351/206 |
| 2015/0216408 A1 | 8/2015 | Brown et al. | | |
| 2016/0089016 A1* | 3/2016 | Shibata | ................ | A61B 3/0025 |
| | | | | 351/206 |
| 2016/0278635 A1* | 9/2016 | Fukuma | ................ | A61B 3/132 |

FOREIGN PATENT DOCUMENTS

| | | |
|---|---|---|
| JP | 2006-122160 A | 5/2006 |
| JP | 2008-206684 A | 9/2008 |
| JP | 2008-237237 A | 10/2008 |
| JP | 2009-000354 A | 1/2009 |
| JP | 2016-043155 A | 4/2016 |
| WO | 2016/178298 A1 | 11/2016 |

* cited by examiner

OPHTHALMIC APPARATUS

CROSS-REFERENCE TO RELATED APPLICATIONS

This application is based union and claims the benefit of priority from Japanese Patent Application No. 2017-186663, filed Sep. 27, 2017; the entire contents of which are incorporated herein by reference.

FIELD

Embodiments described herein relate to an ophthalmic apparatus.

BACKGROUND

Importance of diagnostic imaging and image analysis is increasing in ophthalmic examinations. In particular, the application of optical coherence tomography (OCT) to ophthalmology is spurring this trend. The OCT enables three dimensional imaging, three dimensional structural analysis and functional analysis of a subject's eye, and serves an effective role for acquiring distribution of various measurement values, for example. Distribution of the thickness of a layer tissue of eye fundus is an example of the distribution of the measurement values. The layer thickness distribution acquired for the subject's eye is compared with data of normal eyes (healthy eyes, healthy-seeming eyes) in order to determine the presence or absence of a disease. The normal eye data is referred to as normative data.

The accuracy of fundus structural analysis such as layer thickness distribution analysis is influenced by a magnification error caused by the subject's eye. For example, normative data comparative analysis addresses layer thickness distribution in a predetermined area of an eye fundus. As a specific example, glaucoma diagnosis deals with thickness distribution of a layer (e.g., nerve fiber layer, ganglion cell layer) in a predetermined area around the optic nerve head and thickness distribution of a layer (e.g., nerve fiber layer, ganglion cell layer) in a predetermined area including the fovea centralis. Here, the predetermined areas have preset sizes. A typical size of the areas are 6 mm×6 mm or 9 mm×9 mm.

In order to favorably perform such analysis, it is necessary to apply OCT scan to the predetermined area of an eye fundus. However, even if OCT scan is performed under a fixed scan condition, the area in the eye fundus actually scanned varies depending on the axial length and the refractive power (diopter) of the subject's eye.

For example, as shown in FIG. 1, when OCT measurement light is incident at the fixed angle θ on the subject's eye E1 with the axial length L1 and on the subject's eye E2 with the axial length L2 (>L1), the height Y2 of the projection position of the measurement light on the fundus of the subject's eye E2 is larger than the height Y1 of the projection position of the measurement light on the fundus of the subject's eye E1 (Y2>Y1). As understood from this, the longer the axial length is, the larger the height of the projection position of the measurement light on the fundus becomes. The size of OCT scan is defined by the maximum deflection angle of measurement light. Therefore, even if the size condition of OCT scan is fixed, the area in eye fundus actually scanned changes according to axial length values. The same is true for diopters of subject's eyes.

In nonnative data comparative analysis, normative data for a predetermined area of eye fundus (i.e., for an area of a predetermined size) is prepared. The normative data is, for example, data in which standard values of layer thickness of normal eyes are respectively assigned to a plurality of regions obtained by dividing the predetermined area of funduses of standard eyes. Here, each of the standard values of the layer thickness of the normal eyes is, for example, an average value in the corresponding region. Such normative data and layer thickness distribution acquired for the subject's eye are compared with each other for each of the plurality of regions described above. In addition, a statistical value calculated from the layer thickness distribution of the subject's eye can be compared with the nonnative data. The statistical value may be, for example, a maximum value, a minimum value, an average value, a mode value, a median value, a range (a difference between the maximal value and the minimum value), a standard deviation, or a variance.

For example, thinning (or loss) of nerve fiber layer may appear in glaucomatous eyes, and normative data defines a threshold value for detecting the thinning of nerve fiber layer. When the axial length of the subject's eye belongs to the standard range, the definition area of the normative data and the area of the layer thickness distribution acquired for the subject's eye substantially agree with each other. Therefore, the comparison between both areas can be preferably performed.

On the other hand, for a subject's eye (E2) whose axial length is longer than the standard, as shown in FIG. 2A, the area A2 of the layer thickness distribution acquired for the subject's eye becomes wider than the definition area A0 of the normative data. Considering that the values of the nerve fiber layer thickness is decreasing toward the periphery of the fundus in general, the comparison result indicating "thinning" is obtained even in the event that the nerve fiber layer of the subject's eye is not actually thinning (false positive) since the area A2 includes a site, located outside the original area A0, whose layer thickness is originally thin.

Conversely, in the subject's eye whose axial length is shorter than the standard, as shown in FIG. 2B, the area A3 of the layer thickness distribution acquired for the subject's eye becomes narrower than the definition area A0 of the normative data. Therefore, the comparison result indicating "not thinning" is obtained even in the event that the nerve fiber layer of the subject's eye is actually thinning (false negative).

In order to prevent such false determination, magnification correction techniques for OCT based on ocular optical system parameters (eyeball optical system parameters) such as eye refractive power, corneal curvature radius or axial length have been proposed. Such techniques are disclosed in, for example, Japanese Unexamined Patent Application Publication No. Hei 10-179517 (No. 1998-179517), Japanese Unexamined Patent Application Publication No. 2006-122160, Japanese Unexamined Patent Application Publication No. 2008-206684, Japanese Unexamined Patent Application Publication No. 2009-000354, Japanese Unexamined Patent Application Publication No. 2016-043155, Japanese Unexamined Patent Application Publication No. Hei 08-206081 (No. 1996-206081), and Japanese Unexamined Patent Application Publication No. 2008-237237. However, such conventional techniques perform the magnification correction using data acquired by an ophthalmic apparatus (an external device) other than an apparatus that acquires OCT data. Therefore, there is a problem that the conventional techniques cannot be applied to screening examinations such as health check and to examinations performed at facilities that do not have the above external device.

DETAILED DESCRIPTION

Figure 1:
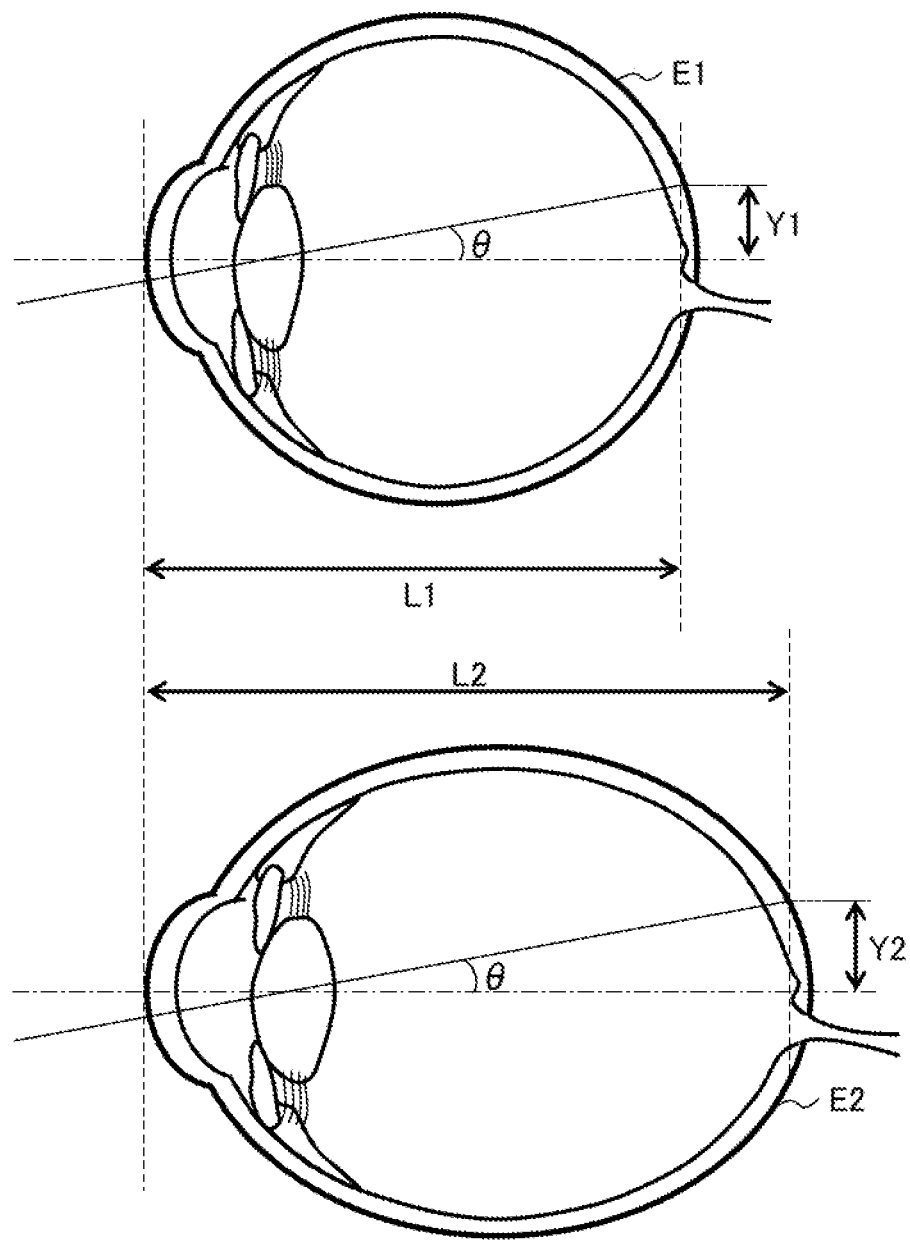
FIG. 1 is a schematic diagram for describing the background.
Figure 2A:
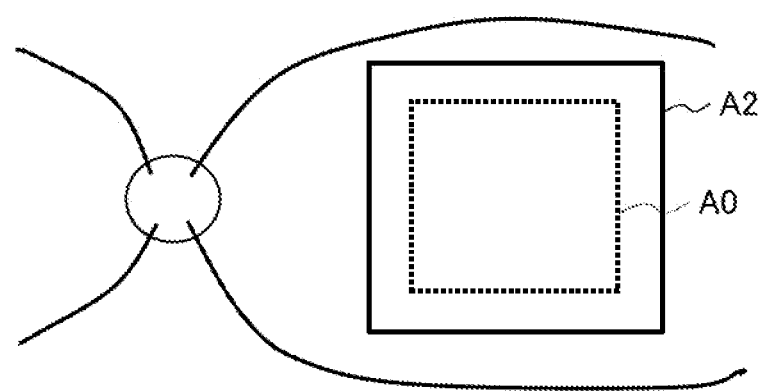
FIG. 2A is a schematic diagram for describing the background.
Figure 2B:
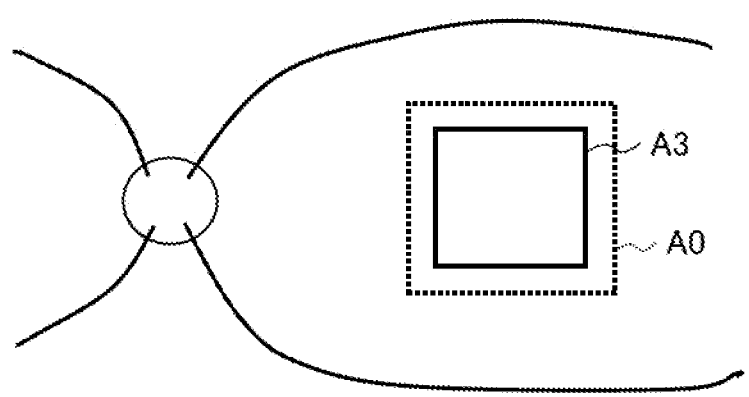
FIG. 2B is a schematic diagram for describing the background.

The first aspect of exemplary embodiments is an ophthalmic apparatus that is capable of applying optical coherence tomography (OCT) to a fundus of a subject's eye, and includes an optical system, an optical scanner, an optical path length changing device, and a controller. The optical system splits light output from a light source into measurement light and reference light, projects the measurement light onto the fundus, generates interference light by superposing returning light of the measurement light from the subject's eye on the reference light, and detects the interference light. The optical scanner deflects the measurement light for scanning the fundus. The optical path length changing device changes at least one of an optical path length (OPL) of the measurement light and an optical path length of the reference light. The controller controls the optical scanner based on at least the optical path length.

The second aspect of exemplary embodiments is the ophthalmic apparatus of the first aspect, wherein the controller controls a deflection range of the measurement light by the optical scanner based on at least the optical path length.

The third aspect of exemplary embodiments is the ophthalmic apparatus of the second aspect, wherein the optical scanner is capable of deflecting the measurement light in a two dimensional manner, and the controller controls a two dimensional deflection range of the measurement light by the optical scanner based on at least the optical path length.

The fourth aspect of exemplary embodiments is the ophthalmic apparatus of the second or third aspect, wherein the optical path length changing device changes the optical path length of the reference light, and the controller applies a first deflection range when the optical path length of the reference light is equal to or greater than a predetermined threshold value, and applies a second deflection range larger than the first deflection range when the optical path length of the reference light is less than the predetermined threshold value.

The fifth aspect of exemplary embodiments is the ophthalmic apparatus of the second or third aspect, wherein the optical path length changing device changes the optical path length of the measurement light, and the controller applies a third deflection range when the optical path length of the measurement light is equal to or greater than a predetermined threshold value, and applies a fourth deflection range smaller than the third deflection range when the optical path length of the measurement light is less than the predetermined threshold value.

The sixth aspect of exemplary embodiments is the ophthalmic apparatus of the second or third aspect, wherein the controller calculates the deflection range based on at least the optical path length.

The seventh aspect of exemplary embodiments is the ophthalmic apparatus of any of the second to sixth aspects, further including a focus adjustment device for performing focus adjustment of the optical system, wherein the controller performs control of the optical scanner based on the optical path length and a focus state of the optical system.

The eighth aspect of exemplary embodiments is a medical method implemented by the ophthalmic apparatus of any of the first to seventh aspects.

Any of the items described in the following disclosure can be combined with each of the first to eighth aspects of some embodiments.

Hereinafter, an ophthalmic apparatus according to exemplary embodiments will be described in detail with referring to the drawings. The ophthalmic apparatus according to the embodiment can apply OCT to a fundus of a living eye. The data acquired by OCT can be used for image construction, analysis and other purposes. Any known techniques can be incorporated in the embodiments, including any contents of the disclosure of the documents cited in the present specification.

In the exemplary embodiments described below, described are ophthalmic apparatuses capable of measuring the fundus of a living eye using Fourier domain OCT (particularly swept source OCT). The type of OCT is not limited to swept source and may be spectral domain OCT or time domain OCT, for example. The ophthalmic apparatuses according to the embodiments are multifunctional apparatuses that are a combination of an OCT apparatus and a fundus camera (retinal camera). However, any kind of fundus photographing apparatus other than a fundus camera may be combined with an OCT apparatus. Examples of such a fundus photographing apparatus include a scanning laser ophthalmoscope (SLO), a slit lamp microscope, and an ophthalmic microscope for surgery.

<Configuration>

Figure 3:
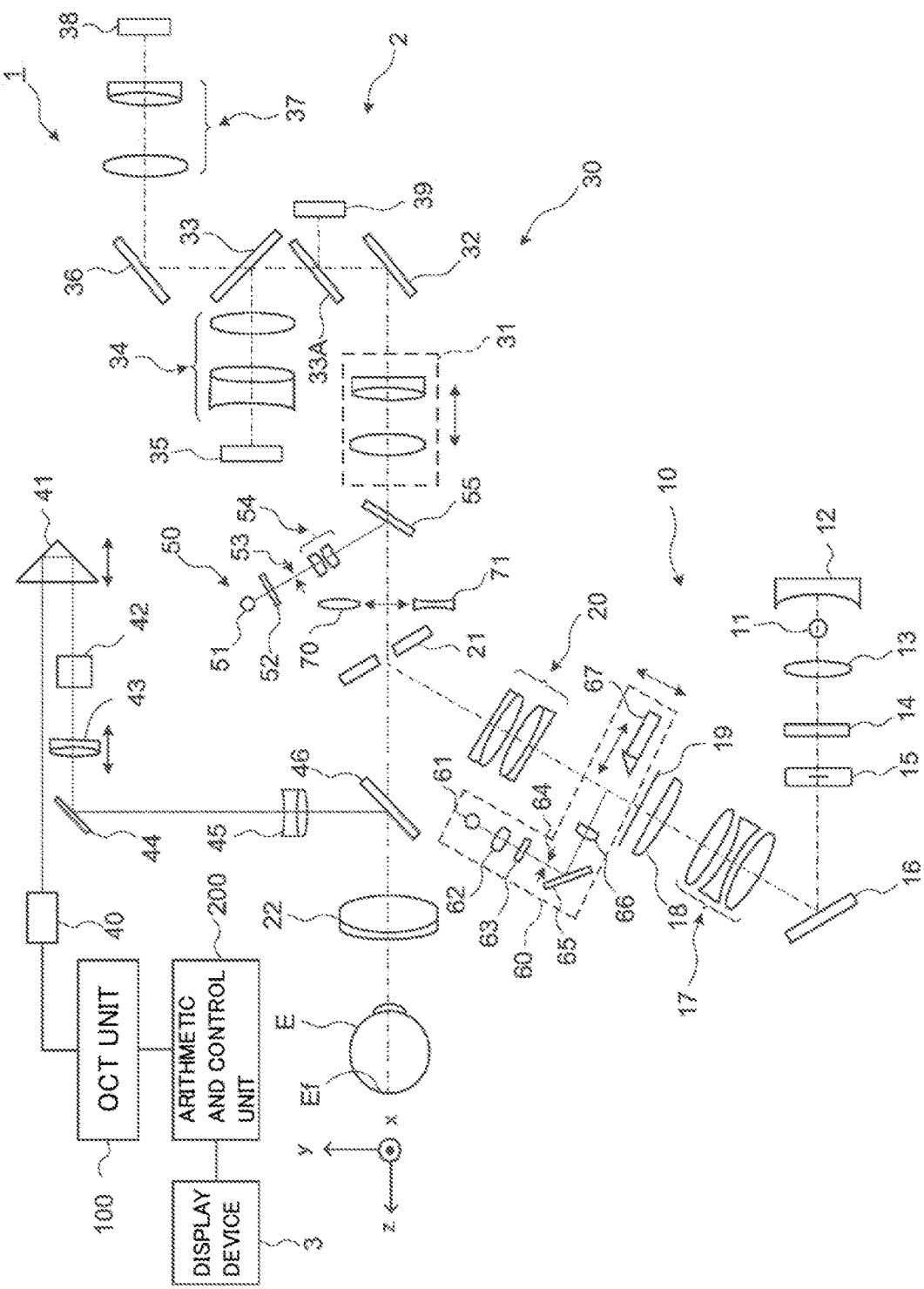
FIG. 3 is a schematic diagram illustrating an example of the configuration of an ophthalmic apparatus according to the embodiment.

As shown in FIG. 3, the ophthalmic apparatus 1 includes the fundus camera unit 2, the OCT unit 100 and the arithmetic and control unit 200. The fundus camera unit 2 is provided with an optical system and a mechanism for acquiring front images of the subject's eye. The OCT unit 100 includes part of an optical system and part of mechanisms for performing OCT. Another part of the optical system and another part of the mechanisms for performing OCT are provided in the fundus camera unit 2. The arithmetic and control unit 200 includes one or more processors that execute various calculations and controls. In addition to these, the ophthalmic apparatus 1 may also include any elements or units such as a member for supporting the face of the subject (e.g., a chin rest, a forehead rest) and a lens unit for switching the sites subjected to OCT imaging (e.g., an attachment for an anterior eye segment OCT).

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the fundus Ef of the subject's eye E. Images of fundus Ef (referred to as fundus images, fundus photographs, or the like) obtained include front images such as observation images and photographed images. An observation image is obtained by capturing a moving image using near-infrared light. A photographed image is a still image obtained by using flash light in the visible range.

The fundus camera unit 2 includes the illumination optical system 10 and the photographing optical system 30. The illumination optical system 10 projects illumination light onto the subject's eye E. The photographing optical system 30 detects the returning light of the illumination light from the subject's eye E. The measurement light incident from the OCT unit 100 is directed to the subject's eye E through the optical path in the fundus camera unit 2, and the returning light thereof is directed to the OCT unit 100 through the same optical path.

The light output from the observation light source 11 of the illumination optical system 10 (called observation illumination light) is reflected by the concave mirror 12, passes through the condenser lens 13, and becomes near-infrared light after passing through the visible cut filter 14. Further, the observation illumination light is once converged near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef thereof). The returning light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the returning light passes through the half mirror 33A, is reflected by the dichroic mirror 33, and forms an image on the light receiving surface of the image sensor 35 by the imaging lens 34. The image sensor 35 detects the returning light at a predetermined frame rate. Note that the focus of the photographing optical system 30 is adjusted to coincide with the fundus Ef or the anterior eye segment.

The light output from the photographing light source 15 (called photographing illumination light) passes through the same route as that of the observation illumination light and is projected onto the fundus Ef. The returning light of the photographing illumination light from the subject's eye E passes through the same route as that of the returning light of the observation illumination light, is guided to the dichroic mirror 33, passes through the dichroic mirror 13, is reflected by the mirror 36, and forms an image on the light receiving surface of the image sensor 38 by the imaging lens 37.

The liquid crystal display (LCD) 39 displays a fixation target (fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the followings: a fixation position for acquiring an image centered on the macula; a fixation position for acquiring an image centered on the optic nerve head; a fixation position for acquiring an image centered on the fundus center that is located between the macula and the optic nerve head; and a fixation position for acquiring an image of a site far away from the macula (periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, capable of changing the fixation position, to the subject's eye E is not limited to display devices such as an LCD. For example, a fixation matrix can be adopted in place of a display device. The fixation matrix includes a plurality of light emitting parts (e.g., light emitting diodes) that are disposed in a matrix-like arrangement (in an matrix array). In this case, the fixation position of the subject's eye E by the fixation target can be changed by lighting one (or more) of the plurality of light emitting parts in a selective manner. As another example, the fixation target that is capable of changing the fixation position can be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The returning light of the alignment light from the subject's eye E (the cornea reflection light, etc.) passes through the same route as that of the returning light of the observation illumination light and is guided to the image sensor 35. Based on the received image (called the alignment indicator image), manual alignment and/or automatic alignment can be performed.

As in a conventional case, the alignment indicator image of the present example includes two bright spot images whose positions change according to the alignment state. When the relative position between the subject's eye E and the optical system changes in the xy direction, the two bright spot images are shifted in the xy direction in an integrated manner. When the relative position between the subject's eye E and the optical system changes in the z direction, the relative position (distance) between the two bright spot images changes. When the distance between the subject's eye E and the optical system in the z direction matches a predetermined working distance, the two bright spot images overlap with each other. When the position of the subject's eye E matches the position of the optical system in the xy direction, the two bright spot images are presented within or near a given alignment target. When the distance between the subject's eye E and the optical system in the z direction matches the working distance, and the position of the subject's eye E matches the position of the optical system in the xy direction, the two bright spot images overlap with each other and are presented within the alignment target.

In the automatic alignment; the data processor 230 detects the positions of the two bright spot images, and the main controller 211 controls the movement mechanism 150 (described later) on the basis of the positional relationship between the two bright spot images and the alignment target. In the manual alignment, the main controller 211 displays the two bright spot images together with the observation image of the subject's eye E on the display 241, and the user operates the movement mechanism 150 using the operation device 242 while referring to the two bright spot images displayed.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (called the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The returning light of the focus light from the subject's eye E (the fundus reflection light, etc.) passes through the same route as the returning light of the alignment light and is guided to the image sensor 35. Based on the image (called the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrow in FIG. 3, whereby the length of the measurement arm is changed. The change in the optical path length of the measurement arm can be utilized for correcting the optical path length according to the axial length, and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is moved along the measurement arm in order to perform the focus adjustment of the measurement arm. The movement of the photography focusing lens 31, the movement of the focus optical system 60, and the movement of the OCT focusing lens 43 can be controlled in an interlocking manner.

The optical scanner 44 is substantially placed at a position optically conjugate with the pupil of the subject's eye E. The optical scanner 44 deflects the measurement light LS guided through the measurement arm. The optical scanner 44 is, for example, a galvano scanner capable of two dimensional scanning.

<OCT Unit 100>

Figure 4:
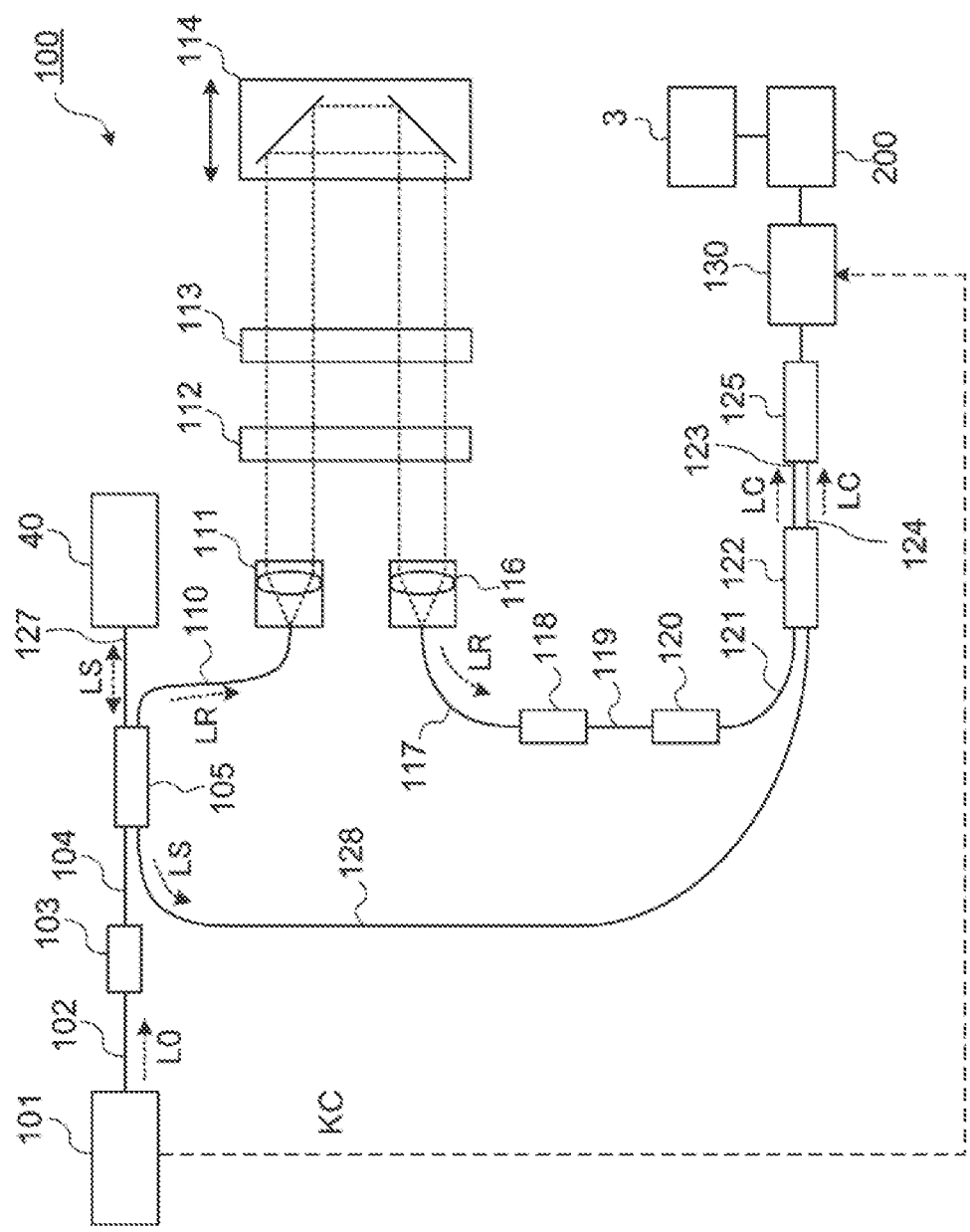
FIG. 4 is a schematic diagram illustrating an example of the configuration of the ophthalmic apparatus according to the embodiment.

As illustrated in FIG. 4, the OCT unit 100 is provided with the optical system for performing swept source OCT. The optical system includes an interference optical system. The interference optical system is configured to split the light emitted from the light source of wavelength tunable type (also called wavelength swept type) into measurement light and reference light, superpose the returning light of the measurement light from the subject's eye E and the reference light having traveled through the reference optical path to generate interference light, and detect the interference light. The detection result (i.e., detection signal) obtained by the interference optical system is a signal representing a spectrum of the interference light. The detection signal is sent to the arithmetic and control unit 200.

The light source unit 101 includes, for example, a near infrared tunable laser configured to change the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the optical path length of the reference arm can be utilized, for example, for the correction of the optical path length according to the axial length, and for the regulation of the interference condition.

The reference light LR that has passed through the retroreflector 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The returning light of the measurement light LS from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 and the reference light LR incident through the optical fiber 121 with each other, to generate interference light. The fiber coupler 122 splits the generated interference light at a predetermined splitting ratio (e.g., 1 to 1) to generate a pair of interference light LC. The pair of the interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, optically delays one of the two pieces of split light, combines the two pieces of split light, detects the combined light obtained, and generates the clock KC based on the result of the detection of the combined light. The data acquisition system 130 performs the sampling of the detection signal input from the detector 125 based on the clock KC. The data acquisition system 130 sends the result of the sampling of the detection signal from the detector 125 to the arithmetic and control unit 200.

The present example is provided with both an element for changing the optical path length of the measurement arm (e.g., the retroreflector 41) and an element for changing the optical path length of the reference arm (e.g., the retroreflector 114 or a reference mirror). However, only one of these elements may be provided in other embodiments. An element for changing the difference between the optical path length of the measurement arm and the optical path length of the reference arm (i.e., an element for changing the optical path length difference) are not limited to the aforesaid elements, and may be any type of element (e.g., any optical member, any mechanism).

<Control System>

Figure 5:
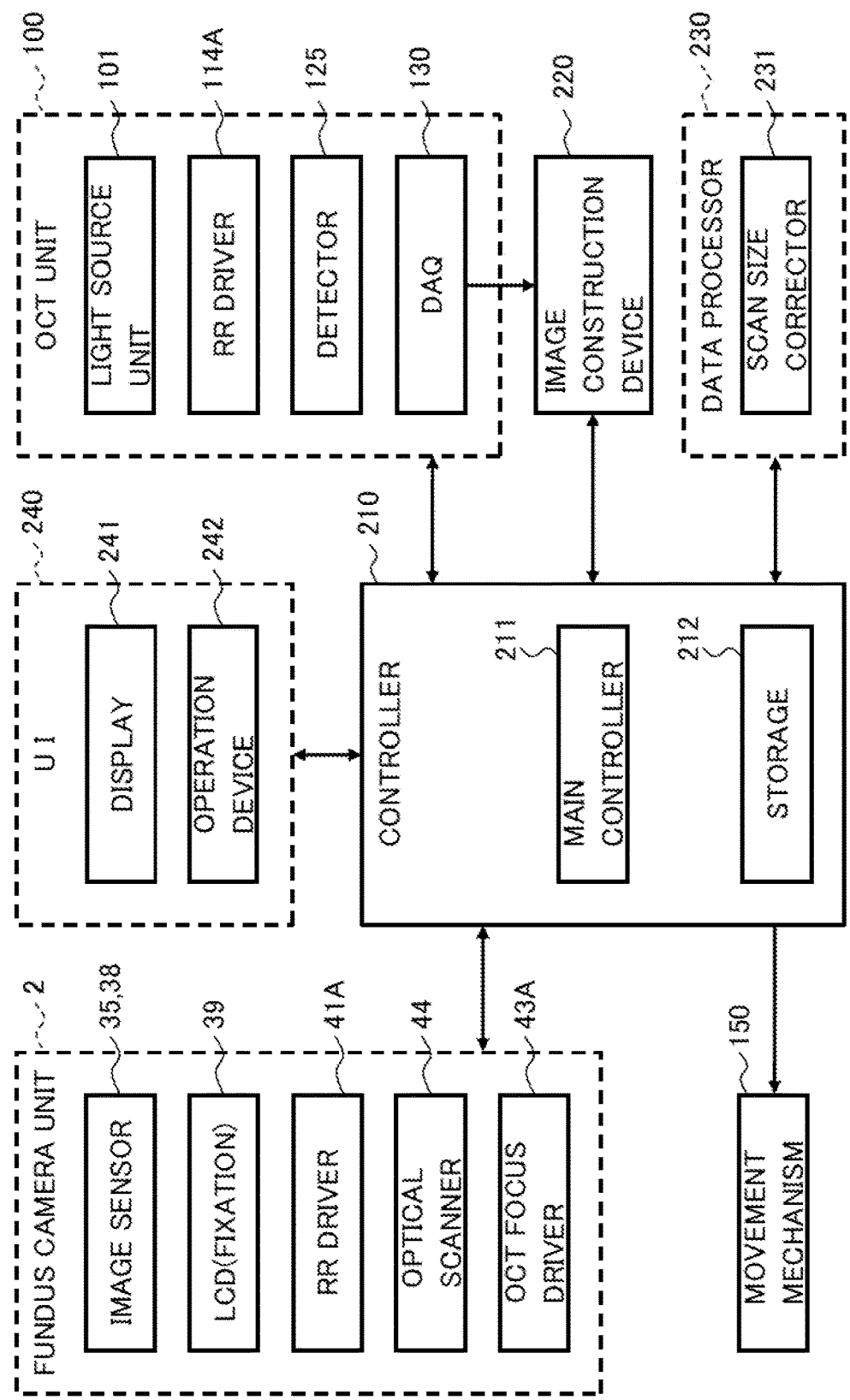
FIG. 5 is a schematic diagram illustrating an example of the configuration of the ophthalmic apparatus according to the embodiment.

FIG. 5 shows an example of the configuration of the control system of the ophthalmic apparatus 1. The controller 210, the image construction device 220 and the data processor 230 are provided, for example, in the arithmetic and control unit 200.

<Controller 210>

The controller 210 performs various kinds of controls. The controller 210 includes the main controller 211 and the storage 212.

<Main Controller 211>

The main controller 211 includes a processor and controls each element of the ophthalmic apparatus 1 (including the elements shown in FIG. 3 to FIG. 5).

The photography focusing lens 31 disposed in the photographing optical path and the focus optical system 60 disposed in the illumination optical path are moved by a photographing focus driver (not shown in figures) under the control of the main controller 211. The retroreflector 41 disposed in the measurement arm is moved by the retroreflector driver (RR driver) 41A under the control of the main controller 211. The OCT focusing lets 43 disposed in the measurement arm is moved by the OCT focus driver 43A under the control of the main controller 211. The optical scanner 44 disposed in the measurement arm operates under the control of the main controller 211. The retroreflector 114 disposed in the reference arm is moved by the retroreflector driver (RR driver) 114A under the control of the main controller 211. Each of the aforesaid drivers includes an actuator such as a pulse motor which operates under the control of the main controller 211.

The movement mechanism 150 moves, for example, at least the fundus camera unit 2 in a three dimensional manner. In a typical example, the movement mechanism 150 includes the followings: an x stage movable in the ±x direction (i.e., left and right direction); an x movement mechanism that moves the x stage; a y stage movable in the ±y direction (i.e., up and down direction); a y movement mechanism that moves the y stage; a z stage movable in the ±z direction (i.e., depth direction); and a z movement mechanism that moves the z stage. Each of the aforesaid movement mechanisms includes an actuator such as a pulse motor which operates under the control of the main controller 211.

<Storage 212>

The storage 212 stores various kinds of data. Examples of the data stored in the storage 212 include OCT images, fundus images, and subject's eye information. The subject's eye information includes subject information such as the patient ID and the patient's name, identification information for the left eye and the right eye, and electronic medical record information.

In the present embodiment, standard distribution data generated in advance is stored in the storage 212. The standard distribution data is data representing a distribution of a predetermined measurement value that can be referred to in diagnostic imaging using OCT and image analysis. The predetermined measurement value is typically the thickness of a predetermined layer tissue of retina. The layer tissue may be nerve fiber layer, ganglion cell layer, or another tissue. However, the predetermined measurement value is not limited to the layer thickness.

The standard distribution data includes, for example, values obtained by statistically processing a sample of the predetermined measurement values acquired from a large number of normal eyes. Typically, the standard distribution data represents a distribution of normal ranges calculated from a sample of layer thickness values obtained by applying OCT to the funduses of a large number of normal eyes. Each of the normal ranges can be set to include, for example, an average value derived from the sample. The standard distribution data generated based on the normal eyes in this way is called normative data. Note that the standard distribution data may be generated based on a plurality of eyes suffering from a specific disease.

The standard distribution data is, for example, a distribution in a predetermined area including a predetermined site of eye fundus. In a typical example, the standard distribution data is generated by assigning a normal range of the layer thickness value of the normal eyes, to each of a plurality of sections that are formed by dividing, in a grid-like manner, a rectangular region of 6 mm×6 mm in which fovea centralis is placed at the center.

The standard distribution data can be prepared for each of two or more diseases and selectively used. The standard distribution data cat be prepared for each of two or more attributes of subjects (e.g., age groups) and selectively used. The standard distribution data can be prepared for each of two or more attributes of subject's eyes (e.g., highly myopic eyes and others) and selectively used.

<Image Construction Device 220>

The image construction device 220 constructs OCT image data of the fundus Ef based on the signal (sampling data) input from the data acquisition system 130. The OCT image data is, for example, B-scan image data (i.e., two dimensional cross sectional image data). The processing for constructing OCT image data includes noise elimination (or noise reduction), filtering, fast Fourier transform (FFT), and other processes as in a conventional Fourier domain OCT. In the event that another type of OCT apparatus is used, the image construction device 220 performs known processing according to the OCT type employed. The image construction device 220 includes a processor. In this specification, "image data" and an "image" formed based on the "image data" may not be distinguished unless otherwise mentioned.

<Data Processor 230>

The data processor 230 executes various kinds of data processing. In a typical example, the data processor 230 applies various kinds of image processing and/or analysis to the image constructed by the image construction device 220. For example, the data processor 230 is configured to be capable of executing various kinds of correction processing such as brightness correction and dispersion correction of an image. Further, the data processor 230 can perform various kinds of image processing and/or various kinds of analysis on an image (e.g., a fundus image, an anterior eye segment image) obtained by the fundus camera unit 2.

The data processor 230 can constrict three dimensional image data of fundus Three dimensional image data means image data in which the positions of pixels are defined using a three dimensional coordinate system. Stack data and volume data are examples of three dimensional image data.

Stack data is image data constructed by arranging a plurality of cross sectional images obtained along a plurality of scan lines in an three dimensional fashion, based on the positional relationship of the scan lines. More specifically, stack data is image data constructed by representing a plurality of cross sectional images, which are originally defined using individual two dimensional coordinate systems, using a common three dimensional coordinate system. In other words, stack data is image data constructed by embedding a plurality of cross sectional images in a single three dimensional space.

Volume data is image data whose picture elements are voxels that are arranged in a three dimensional manner. Volume data is also referred to as voxel data. Volume data is constructed by applying known interpolation, voxelization, or the like, to stack data.

The data processor 230 can construct an image to be displayed, by applying rendering to three dimensional image data. Examples of applicable rendering methods include volume rendering, surface rendering, maximum intensity projection (MIP), minimum intensity projection (MinIP), and multiplanar reconstruction (MPR).

In the present embodiment, a three dimensional scan is applied to the fundus Ef in order to acquire distribution data for normative data comparative analysis. A three dimensional scan is an OCT scan for a three dimensional region in the fundus Ef. The mode of a three dimensional scan may be optional. For example, a raster scan is used as a three dimensional scan. The ophthalmic apparatus 1 (i.e., the image construction device 220 and the data processor 230) processes data acquired through a three dimensional scan (i.e., processes three dimensional data) to construct three dimensional image data. It should be noted that one or both of distribution data generation and normative data comparative analysis may be executed by another apparatus.

The data processor 230 may be configured to generate distribution data of a predetermined measurement value in the fundus Ef based on the three dimensional image data constructed. As described above, the predetermined measurement value is referred to in diagnostic imaging using OCT and image analysis, and is of the same kind as the measurement value represented by the standard distribution data. The predetermined measurement value in the present example is the thickness of a predetermined layer tissue of retina. Examples of the retinal layer tissue include nerve fiber layer and ganglion cell layer. However, the predetermined measurement value is not limited to such layer thickness.

In the present example, the data processor 230 may be configured to generate layer thickness distribution data representing a distribution of the thickness of the predetermined layer tissue in the retina of the fundus Ef. The contents (or details) of the processing executed by the data processor 230 to generate the layer thickness distribution data is optional.

In one example the data processor 230 includes the following processing as with a conventional manner: a process of dividing three dimensional image data into a plurality of pieces of partial image data by applying segmentation to the three dimensional image data; a process of specifying (selecting) the partial image data corresponding to the predetermined layer tissue from among the plurality of pieces of partial image data; and a process of determining (calculating) the thickness of the predetermined layer tissue at each of a plurality of positions, based on the partial image data specified (selected).

<Scan Size Corrector 231>

The data processor 230 includes the scan size corrector 231. As described above, the present embodiment is configured to be capable of changing at least one of the optical path length of the measurement arm and the optical path length of the reference arm. The scan size corrector 231 can determine the maximum deflection angle of the optical scanner 44 based on at least one of the optical path length of the measurement arm and the optical path length of the reference arm. The maximum deflection angle of the optical scanner 44 corresponds to the range (deflection range) within which the optical scanner 44 deflects the measurement light LS.

The controller 210 sends information on the variable optical path lengths) among the optical path length of the measurement arm and the optical path length of the reference arm, to the scan size corrector 231. The information sent to the scan size corrector 231 is referred to as optical path length information. The change in the optical path length of the measurement arm can be performed with the retroreflector 41 and the retroreflector driver 41A. The change in the optical path length of the reference arm can be performed with the retroreflector 114 and the retroreflector driver 114A. Typical embodiments are configured to be capable of changing only either one of the optical path length of the measurement arm and the optical path length of the reference arm.

The optical path length information may include, for example, a parameter value representing the actual length of the optical path, such as the optical distance of an optical path (e.g., the optical path of the measurement arm or the optical path of the reference arm) or the length of an optical path in real space. In addition, the optical path length information may include information substantially equivalent to the actual length of the optical path, such as the position of a member that is moved to change the optical path length, the operation state of a mechanism that moves the member, or the control content for the mechanism.

For example, the optical path length information on the measurement arm may include any of the followings: the position of the retroreflector 41; the operation state of the actuator included in the retroreflector driver 41A; and the content of control (the history of control) executed by the main controller 211 for the retroreflector driver 41A.

The position of the retroreflector 41 or the operation state of the actuator of the retroreflector driver 41A can be detected using a position detector (not shown in figures) such as a potentiometer or an encoder, for example. Alternatively, the position of the retroreflector 41 or the operation state of the actuator of the retroreflector driver 41A may be detected based on the control content (control history) of the main controller 211 for the retroreflector driver 41A. The control content (control history) of the main controller 211 for the retroreflector driver 41A is recorded as a control log by the controller 210, for example.

Positions of the retroreflector 41 or operation states of the actuator of the retroreflector driver 41A can be associated with values of the optical path length of the measurement arm in advance. This association is made, for example, based on the design data of the measurement arm. The association information (e.g., table information, graph information, etc.) representing the association is prepared in advance and stored in the storage 212, for example. The data processor 230 (e.g., the scan size corrector 231) receives a detection result of the position of the retroreflector 41 (or a detection result of the operation state of the actuator of the retroreflector driver 41A), and determines the value of the optical path length corresponding to the received detection result with referring to the association information. The value of the optical path length determined is used as the optical path length of the measurement arm.

Similarly, the optical path length information on the reference arm may include any of the followings: the position of the retroreflector 114; the operation state of the actuator included in the retroreflector driver 114A; and the content of control (the history of control) executed by the main controller 211 for the retroreflector driver 114A.

The position of the retroreflector 114 or the operation state of the actuator of the retroreflector driver 114A is detected using a position detector (not shown in figures) such as a potentiometer or an encoder, for example. Alternatively, the position of the retroreflector 114 or the operation state of the actuator of the retroreflector driver 114A may be detected based on the control content (control history) of the main controller 211 for the retroreflector driver 114A. The control content (control history) of the main controller 211 for the retroreflector driver 114A is recorded as a control log by the controller 210, for example.

Positions of the retroreflector 114 or operation states of the actuator of the retroreflector driver 114A can be associated with values of the optical path length of the reference arm in advance. This association is made, for example, based on the design data of the reference arm. The association information (e.g., table information, graph information, etc.) representing the association is prepared in advance and stored in the storage 212, for example. The data processor 230 (e.g., the scan size corrector 231) receives a detection result of the position of the retroreflector 114 (or a detection result of the operation state of the actuator of the retroreflector driver 114A), and determines the value of the optical path length corresponding to the received detection result with referring to the association information. The value of the optical path length determined is used as the optical path length of the reference arm.

As described above, the scan size corrector 231 determines the maximum deflection angle of the measurement light LS deflected by the optical scanner 44. The maximum deflection angle corresponds to the size of the OCT scan. For example in the case of performing a line scan, the maximum deflection angle corresponds to the length of the scan line. In the case of performing a three dimensional scan, the maximum deflection angle in the x direction corresponds to the dimension (length) in the x direction of the scan area, and the maximum deflection angle in the y direction corresponds to the dimension (length) in the y direction of the scan area. For example, in the case of performing a raster scan consisting of a plurality of scan lines each extending in the x direction that are arranged in the y direction, the maximum deflection angle in the x direction corresponds to the lengths of the plurality of scan lines, and the maximum deflection angle in the y direction corresponds to the distance between the scan lines at both ends in the arrangement of the plurality of scan lines.

In general, for the same subject's eye, (in other words, provided that the axial length and diopter are constant), increase in the maximum deflection angle corresponds to increase in OCT scan size and decrease in the maximum deflection angle corresponds to decrease in OCT scan size. On the other hand, even when the same maximum deflection angle is applied, the area of eye fundus actually scanned varies depending on axial lengths and diopters of subject's eyes.

The present embodiment is configured to change the maximum deflection angle of the optical scanner 44 according to the characteristics (e.g., axial lengths, diopters) of subject's eyes, which makes it possible to scan the areas of eye funduses of substantially the same size without being influenced by the characteristics of the subject's eyes. For example, the present embodiment is capable of applying a line scan to a linear region with a length of 9 mm of eye funduses regardless of the characteristics of subject's eyes. In addition, the present embodiment is capable of applying a raster scan to a rectangular region with a size of 6 mm×6 mm of eye funduses regardless of the characteristics of subject's eyes.

When the optical path length information includes any of the parameter values described above, information for determining the maximum deflection angle can be prepared from the parameter value included in the optical path length information. For example, the entire value range that the parameter can take is divided into two or more sections, and maximum deflection angles can respectively be associated with the sections. For example, a threshold value for the parameter can be set, and a maximum deflection angle can be associated with a section of values equal to or greater than the threshold value, and another maximum deflection angle can be associated with a section of values less than the threshold value.

When the optical path length of the reference arm is adjusted according to the subject's eye, the longer the axial length is, the longer the optical path length of the reference arm is set. Further, provided that the maximum deflection angle (deflection range) is constant, the longer the axial length is, the wider the area of eye fundus actually scanned becomes (see FIG. 1). In consideration of such facts, the following information can be prepared.

That is, when the optical path length of the reference arm is changed, the first maximum deflection angle (the first deflection range) may be associated with the section in which the optical path length of the reference arm (or the value of the parameter substantially equivalent to the optical path length of the reference arm) is equal to or greater than the threshold value, and the second maximum deflection angle (the second deflection range) may be associated with the section in which the optical path length of the reference arm (or the value of the parameter substantially equivalent to the optical path length of the reference arm) is less than the threshold value. Here, the second maximum deflection angle is set to be larger than the first maximum deflection angle. It should be noted that three or more maximum deflection angles (deflection ranges) corresponding to three or more sections can be set in other examples.

Conversely, when the optical path length of the measurement arm is adjusted according to the subject's eye, the longer the axial length is, the shorter the optical path length of the measurement arm is set. In the case where the optical path length of the measurement arm is changed, the third maximum deflection angle (the third deflection range) may be associated with the section in which the optical path length of the measurement arm (or the value of the parameter substantially equivalent to the optical path length of the measurement arm) is equal to or greater than the threshold value, and the fourth maximum deflection angle (the fourth deflection range) may be associated with the section in which the optical path length of the measurement arm (or the value of the parameter substantially equivalent to the optical path length of the measurement arm) is less than the threshold value. Here, the fourth maximum deflection angle is set to be smaller than the third maximum deflection angle. It should be noted that three or more maximum deflection angles (deflection ranges) corresponding to three or more sections can be set in other examples.

As another example of the information prepared for determining the maximum deflection angle from the parameter value included in the optical path length information is information for calculating the maximum deflection angle (deflection range) based on the optical path length. This information may be, for example, a formula (mathematical relationship) whose independent variable is the optical path length and whose dependent variable is the maximum deflection angle (deflection range). Here, the optical path length as the independent variable may be, for example, the optical path length of the reference arm or the optical path length of the measurement arm, or a parameter substantially equivalent to the optical path length of the reference arm or the optical path length of the measurement arm. Alternatively, any other type of association, such as a graph or a lookup table, may be prepared in place of a mathematical formula.

Thus far, the cases have been described where the parameter value included in the optical path length information is used, as it is, for acquiring the maximum deflection angle (deflection range). However, the embodiment is not limited thereto. For example, another embodiment may be configured to obtain information of other type from the parameter value included in the optical path length information and determine the maximum deflection angle (deflection range) based on the information of other type obtained.

In a typical example, the scan size corrector 231 can calculate an estimated value of the axial length of the subject's eye E, and determine a maximum deflection angle (deflection range) based on the estimated value calculated. In this case, information of any form (e.g., arithmetic formula, graph, lookup table, etc.) that associates axial length values (or values of a parameter substantially equivalent to axial length) and maximum deflection angle values (deflection ranges) with each other is prepared, and a maximum deflection angle value (deflection range) is determined based on this information and the estimated value calculated.

The calculation of the estimated value of the axial length will be described. As an example, the method described in Japanese Unexamined Patent Application Publication No. 2008-237237 can be applied. More specifically, given that the optical path length of the reference arm is denoted by $OPL_R$, the optical path length of the measurement arm is denoted by $OPL_S$, the working distance is denoted by WD, and the intraocular distance between the position where the measurement light LS is incident on the subject's eye E and the position where the measurement light LS is reflected at the fundus Ef is denoted by D, there is the following relationship between these parameters: $OPL_R = OPL_S + WD + D$. From this, the intraocular distance D (that is, the estimated value of the axial length D) can be expressed as follows: $D = OPL_R - OPL_S - WD$.

When the alignment of the optical system of the ophthalmic apparatus 1 with respect to the subject's eye E has been performed in a proper manner, the optical system (the objective lens 22) is located at a position away from the subject's eye E by the preset working distance WD in the −z direction. As such, in the present example, the working distance WD is a preset constant, and on condition that the alignment has been completed (furthermore, the subsequent tracking has been performed in an appropriate manner), it is assumed that the distance between the optical system and the subject's eye E is equal to the working distance WD, and the constant WD is applied. In the present example, the working distance WD corresponds to the condition related to alignment.

The condition related to alignment is not limited to such a default value of working distance. For example, when a configuration that is capable of determining the distance (the distance in the z direction) between the subject's eye E and the optical system is adopted, as in the case of performing alignment using two or more cameras that are capable of imaging the subject's eye E front mutually different directions, the value of the distance thus determined can be used as the condition related to alignment instead of the working distance WD.

In general, prior to applying an OCT scan to the fundus Ef, the optical path length adjustment of the interference optical system is performed so that an image of the fundus Ef is displayed at a predetermined position in the frame of an OCT image. More specifically, at least one of the optical path length of the measurement arm and the optical path length of the reference arm is adjusted. The change in the optical path length of the measurement arm can be performed by the retroreflector 41 and the retroreflector driver 41A under the control of the main controller 211, for example. The change in the optical path length of the reference arm can be performed by the retroreflector 114 and the retroreflector driver 114A under the control of the main controller 211.

The position of the retroreflector 41 or the operation state of the actuator of the retroreflector driver 41A is detected using a position detector (not shown in figures) such as a potentiometer or an encoder, for example. Alternatively, the position of the retroreflector 41 or the operation state of the actuator of the retroreflector driver 41A may be detected based on the control content (control history) of the main controller 211 for the retroreflector driver 41A.

Positions of the retroreflector 41 or operation states of the actuator of the retroreflector driver 41A can be associated with values of the optical path length of the measurement arm in advance. This association is made, for example, based on the design data of the measurement arm. The association information (e.g., table information, graph information, etc.) representing the association is prepared in advance and stored in the storage 212, for example. The scan size corrector 231 receives a detection result of the position of the retroreflector 41 (or a detection result of the operation state of the actuator of the retroreflector driver 41A), and determines the value of the optical path length corresponding to the received detection result with referring to the association information. The value of the optical path length determined is used as the optical path length of the measurement arm $OPL_S$.

The optical path length of the reference arm $OPL_R$ can be determined in that same manner. The optical path length of the reference arm $OPL_R$ and the optical path length of the measurement arm $OPL_S$ correspond to the condition related to the OCT optical path length.

When only either one of the optical path length of the measurement arm and the optical path length of the reference arm can be varied, the optical path length of one arm whose optical path length can be changed is calculated, for example, in the manner described above. In addition, a preset value (design data) is applied as the optical path length of the other arm whose optical path length is fixed.

The scan size corrector 231 can calculate the estimated value of the axial length D by substituting the optical path length of the reference arm $OPL_R$, the optical path length of the measurement arm $OPL_S$, and the working distance WD into the above arithmetic formula "$D=OPL_R-OPL_S-WD$". Then, the scan size corrector 231 can determine the maximum deflection angle (deflection range) based on the estimated value D calculated and the information prepared (e.g., arithmetic formula, graph, lookup table).

In addition to or instead of the optical path length information or the information obtained therefrom (e.g., an estimated value of the axial length), focus information may be utilized or information derived from focus information (e.g., an estimated value of the diopter, etc.) may be utilized.

The focus information may include a value of parameter representing the focus state of the measurement arm. For example, the focus information includes the position of a member that is moved to change the focus state of the measurement arm, the operation state of a mechanism that moves the member, or the control content for the mechanism. As a typical example, the focus information may include any of the followings: the position of the OCT focusing lens 43; the operation state of the actuator included in the OCT focus driver 43A; and the content of control (the history of control) executed by the main controller 211 for the OCT focus driver 43A.

The position of the OCT focusing lens 43 or the operation state of the actuator of the OCT focus driver 43A can be detected using a position detector (not shown in figures) such as a potentiometer or an encoder, for example. Alternatively, the position of the OCT focusing lens 43 or the operation state of the actuator of the OCT focus driver 43A may be detected based on the control content (control history) of the main controller 211 for the OCT focus driver 43A. The control content (control history) of the main controller 211 for the OCT focus driver 43A is recorded as a control log by the controller 210, for example.

When the main controller 211 is configured to control the movement of the photography focusing lens 31 and the movement of the OCT focusing lens 43 in an interlocking manner, the focus information may include the position of the photography focusing lens 31, the operation state of a photographing focus driver (not shown in figures), and the control content (control history) of the main controller 211 for the photographing focus driver.

An example of the information that can be obtained from the focus information as exemplified above is an estimated value of the diopter. In general, before applying an OCT scan to the fundus Ef, the OCT focusing lens 43 disposed in the measurement arm is moved by the OCT focus driver 43A under the control of the main controller 211 according to the diopter (refractive power) of the subject's eye E. This processing is carried out, for example, based on the result of the autofocusing of the fundus camera unit 2 using the split indicator (that is, the automatic movement of the photography focusing lens 31 and the focus optical system 60). For example, the autofocusing according to the present embodiment is performed by interlocking controls of the movement of the photography focusing lens 31, the movement of the focusing optical system 60, and the movement of the OCT focusing lens 43, as in a conventional case.

As described above, the position of the OCT focusing lens 43 or the operation state of the OCT focus driver 43A (or, the position of the photography focusing lens 31 or the operation state of the photographing focus driver (not shown in figures)) is detected using, for example, a position detector (not shown in figures) such as a potentiometer or an encoder. Alternatively, the position of the OCT focusing lens 43 or the operation state of the OCT focus driver 43A (or, the position of the photography focusing lens 31 or the operation state of the photographing focus driver (not shown in figures)) can be detected based on the control content (control history) of the main controller 211 for the OCT focus driver 43A (or for the photographing focus driver). In addition, in the case where the photography focusing lens 31 and the OCT focusing lens 43 are configured to be controlled and operated independently of each other, the movement destination of the OCT focusing lens 43 can be determined on the basis of an evaluation value (e.g., contrast) of an image obtained by a preliminary scan.

Further, positions of the OCT focusing lens 43 or operation states of the actuator of the OCT focus driver 43A (or, positions of the photography focusing lens 31 or operation states of the actuator of the photographing focus driver) can be associated in advance with values of the diopters of eyes. This association is made, for example, based on the design data of the optical system (the measurement arm or the imaging optical system 30). The association information (e.g., table information, graph information, etc.) representing the association is prepared in advance and stored in the storage 212, for example. The scan size corrector 231 receives a detection result of the position of the OCT focusing lens 43 (or, a detection result of the operation state of the actuator of the OCT focus driver 43A, a detection result of the position of the photography focusing lens 31, or a detection result of the operation state of the actuator of the photographing focus driver). Further the scan size corrector 231 determines the value of the diopter corresponding to the received detection result with referring to the association information. The value of the diopter determined is used as an estimated value of the diopter of the subject's eye E.

In this manner, the scan size corrector 231 can determine at least one of the estimated value of the axial length and the estimated value of the diopter, from a predetermined condition for acquiring the three dimensional data of the fundus Ef by the three dimensional OCT scan. Note that an estimated value that can be calculated by the scan size corrector 231 is not limited to the estimated value of the axial length and the estimated value of the diopter. The scan size corrector 231 may calculate an estimated value of any characteristic of the subject's eye E that can be used for scan size correction such as scan line length correction or scan area size correction.

In the same manner as in the case of correcting the scan size based on the optical path length information and/or information obtained from the optical path length information (e.g., an estimated value of the axial length), the scan size corrector 231 can correct the scan size on the basis of the focus information and/or information obtained from the focus information (e.g., an estimated value of the diopter). Alternatively, the scan size corrector 231 may be configured to correct the scan size based on the optical path length information and/or information obtained from the optical path length information as well as the focus information and/or information obtained from the focus information.

Further, the scan size corrector 231 can calculate a parameter value (a magnification correction value) for correcting the scan size based on one or more estimated values calculated from predetermined conditions applied in the acquisition of three dimensional data. This processing is executed by using the magnification calculation method described in, for example Japanese Unexamined Patent Application Publication No. 2008-206684 or Japanese Unexamined Patent Application Publication No. 2016-043155.

The magnification correction value is calculated as a value defined on the basis of a predetermined reference value. The reference value may be, for example, a value according to the size of the normative data (e.g., 6 mm×6 mm) prepared in advance. In this case, the maximum deflection angle (the deflection range) in the x direction and the maximum deflection angle (the deflection range) in the y direction of the optical scanner 44 are set so that a three dimensional scan applied to the fundus Ef is performed with the target of an area of [size in the x direction is 6 mm]×[size in they direction is 6 mm].

By setting the maximum deflection angles in this manner, it becomes possible to actually scan a region of a predetermined size in the fundus Ef regardless of the axial length and the diopter of the subject's eye E.

Note that in the calculation of the magnification correction value, an eye characteristic value different from the one or more estimated values described above can be used. The corneal curvature radius and the intraocular lens power are examples of the eye characteristic value different from the aforesaid estimated values. The eye characteristic value may be, for example, a value acquired by the ophthalmic apparatus 1, a standard value from a model eye etc., or other default values.

<Operation>

Figure 6:
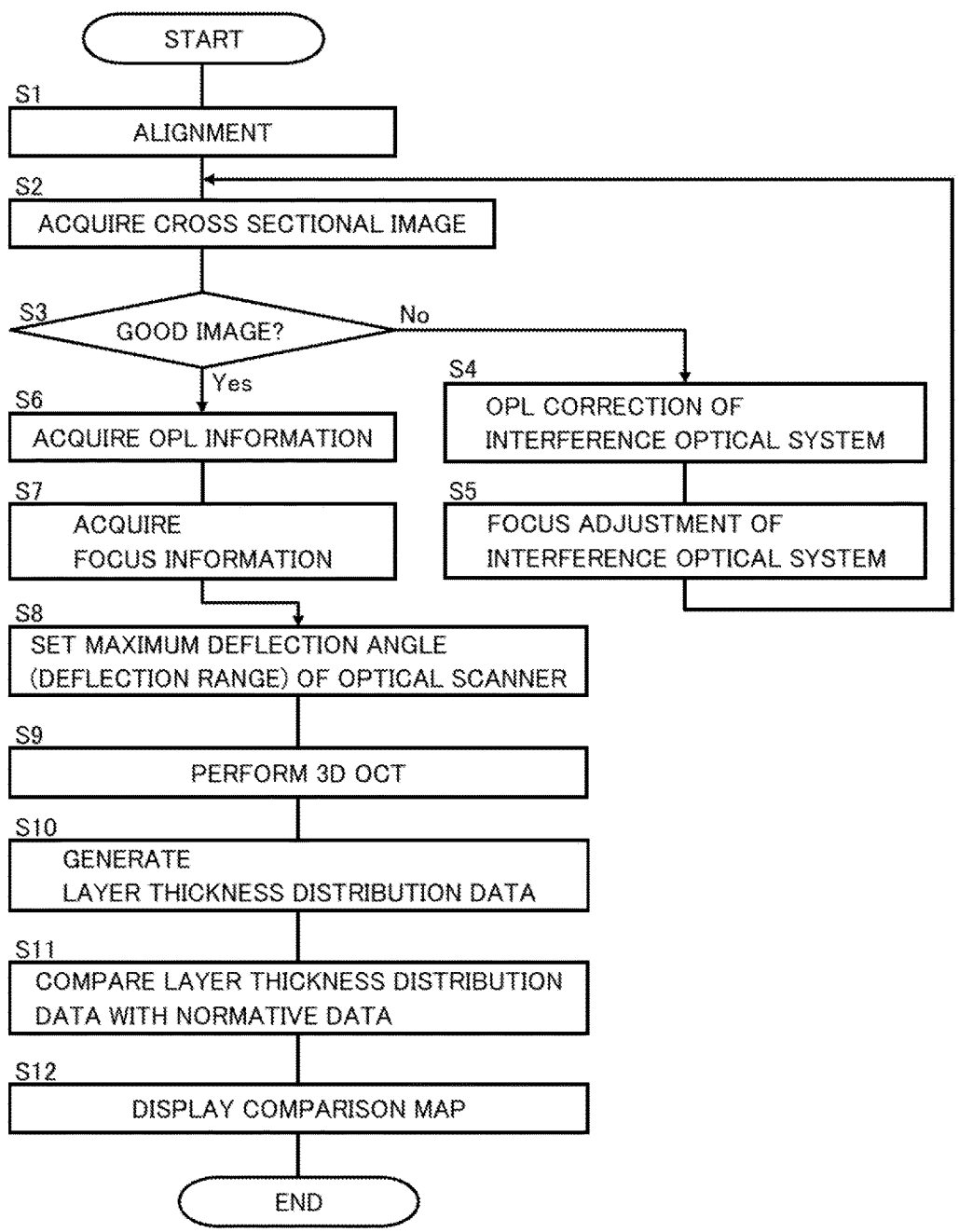
FIG. 6 is a flowchart illustrating an example of the operation of the ophthalmic apparatus according to the embodiment.

The operation of the ophthalmic apparatus 1 will be described. FIG. 6 shows an example of the operation of the ophthalmic apparatus 1. Any preliminary process similar to conventional methods such as the input of a patient ID, the presentation of a fixation target, and the adjustment of the fixation position may be performed at any stage (at any timing).

(S1: Alignment)

First, the ophthalmic apparatus 1 performs alignment of the optical system with respect to the subject's eye E. In a typical example, automatic alignment using the alignment indicator is executed. Here, the focus adjustment of the interference optical system (the measurement arm) may be further performed.

(S2: Acquire Cross Sectional Image)

Upon completion of the alignment in step S1, the ophthalmic apparatus 1 acquires a cross sectional image by applying OCT to the fundus Ef. This process includes: a scanning step of applying an OCT scan of a predetermined scan mode to the fundus Ef; and an image constructing step of constructing a cross sectional image from the data acquired by the OCT scan. The scanning step is executed by the main controller 211 by controlling the OCT unit 100, the optical scanner 44, and other elements.

The seat anode applied to the OCT scan in step S2 is, for example, a B-scan that passes through a region in the fundus Ef to which a three dimensional OCT scan is to be applied in the subsequent step S9. As an example, when the application area of the three dimensional OCT scan is a region of 6 mm×6 mm area centering on the fovea centralis, the location of the B-scan can be set so as to pass through the center position of the region. Further, the number of B-scans may be any number equal to one or larger. For example, a horizontal scan (a B-scan along the x direction) and a vertical scan (a B-scan along the y direction), each of which passes through the center position of the application area of the three dimensional OCT scan, can be performed. This means that the scan mode may be a cross scan.

It should be noted that the scan mode applied to the OCT scan in step S2 is not limited to a B-scan or a combination of two or more B-scans. For example, any scan mode such as a circle scan or a three dimensional scan can be applied to the OCT scan in step S2.

(S3: Is this Good Cross Sectional Image?)

The ophthalmic apparatus 1 (for example, the data processor 230) determines whether or not a good cross sectional image has been acquired in step S2. This determination process may include, for example, at least the determination of the position of the image of the predetermined tissue of the fundus Ef in the frame (in particular, the position in the z direction), and may further include the determination of the interference intensity, the determination of the image quality, or other kinds of determination. The predetermined tissue subject to the position determination is, for example, the surface of the fundus Ef (i.e., the inner limiting membrane). The determination processes may be carried out in the same manner as conventional determinations.

When it is determined that a good cross sectional image has not been acquired (S3: No), the process proceeds to step S4. On the other hand, when it is determined that a good cross sectional image has been acquired (S3: Yes), the process proceeds to step S6.

(S4: Correct Optical Path Length of Interference Optical System)

When it is determined in step S3 that a good cross sectional image has not been acquired (S3: No), the main controller 211 executes at least one of the optical path length correction for the measurement arm and the optical path length correction for the reference arm. The optical path length correction is executed so that an image of a predetermined tissue of the fundus Ef is depicted within a predetermined area of the frame.

The correction amount of the optical path length is calculated by the data processor 230, based on the positional relationship between the depicted position of the predetermined tissue of the fundus Ef and the predetermined area of the frame, for example. In other words, the correction amount corresponding to the deviation (shift) of the depicted position of the predetermined tissue of the fundus Ef with respect to the predetermined area of the frame is calculated.

The optical path length correction for the measurement arm is performed by the main controller 211 controlling the retroreflector driver 41A for moving the retroreflector 41. Further, the optical path length correction for the reference arm is performed by the main controller 211 controlling the retroreflector driver 114A for moving the retroreflector 114.

(S5: Adjust Focus of Interference Optical System)

Next, the main controller 211 performs focus adjustment of the measurement arm. The focus adjustment is performed using, for example, a result of the abovementioned determination of the interference intensity, a result of the abovementioned determination of the image quality, or another determination. The focus adjustment may be performed by using the split indicator.

When the optical path length correction and the focus adjustment of the interference optical system have been performed, the process returns to step S2 to acquire a new cross sectional image, and then the determination whether the new cross sectional image is good or not is performed. Steps S2 to S5 may be repeated until the determination result "Yes" is obtained in step S3. Note that it may be configured to output an imaging error when the number of repetitious of the steps has reached a predetermined number of times or when the execution time of the repetition reaches a predetermined time. When an imaging error has been output, for example, the ophthalmic apparatus 1 can perform the processing again front step S1 or shift to manual adjustment.

(S6: Acquire Optical Path Length Information)

When it is determined in step S3 that a good cross sectional image has been acquired (S3: Yes), the main controller 211 acquires the optical path length of the interference optical system (i.e., at least one of the optical path length of the measurement arm and the optical path length of the reference arm) applied in the acquisition of the cross sectional image.

When the optical path length of the measurement arm is variable, for example, the optical path length of the measurement arm is determined based on the position of the retroreflector 41 at the time of the acquisition of the cross sectional image that has been determined to be good. Similarly, when the optical path length of the reference arm is variable, for example, the optical path length of the reference arm is determined based on the position of the retroreflector 141 at the time of the acquisition of the cross sectional image that has been determined to be good. When the optical path length of the measurement arm (or the optical path length of the reference arm) is fixed, for example, the value of the fixed optical path length stored in advance in the storage 212 is referred to.

(S7: Acquire Focus Information)

Further, the main controller 211 detects the position of the OCT focusing lens 43 at the time of the acquisition of the cross sectional image that has been determined to be good. When the movement of the OCT focusing lens 43, the movement of the photography focusing lens 31, and the movement of the focus optical system 60 are executed in an interlocking manner, the position of the OCT focusing lens 43 may be obtained from the position of the photography focusing lens 31 (or, from the position of the focus optical system 60).

The detection of the position of the OCT focusing lens 43 may be the detection of the position of the OCT focusing lens 43 itself or the detection of the operation state of the actuator of the OCT focus driver 43A. The same also applies to the detection of the position of the photography focusing lens 31 and the detection of the position of the focus optical system 60.

(S8: Set Maximum Deflection Angle (Deflection Range) of Optical Scanner)

The scan size corrector 231 determines the maximum deflection angle (deflection range) of the optical scanner 44 based on at least one of the optical path length information acquired in step S6 and the focus information acquired in step S7. Any one of the processing examples described above may be applied to the maximum deflection angle determination. The main controller 211 sets the maximum deflection angle determined by the scan size corrector 231 as the scan condition to be applied to the next step S9.

(S9: Perform Three Dimensional OCT)

The ophthalmic apparatus 1 applies the three dimensional OCT to the fundus Ef under the scan condition including the maximum deflection angle (deflection range) set in step S8. Thereby, three dimensional image data of the fundus Ef is acquired. This processing includes, for example the following steps: a scanning step of applying an OCT scan to the fundus Ef under conditions including the maximum deflection angle (deflection range) set in step S8 and a predetermined three dimensional scan mode (e.g., a raster scan); and an image constructing step of constructing three dimensional image data from the three dimensional data acquired by the OCT scan performed in the scanning step.

(S10: Generate Layer Thickness Distribution Data)

The data processor 230 generates layer thickness distribution data based on the three dimensional image data acquired in step S9.

(S11: Compare Layer Thickness Distribution Data and Normative Data)

The data processor (data comparator) 230 compares the layer thickness distribution data generated in step S10 with the normative data prepared in advance.

In the present example, step S9 obtains data of a region in the fundus Ef having substantially the same size as the normative data (e.g., size of 6 mm×6 mm), or, step S9 obtains data of a region in the fundus Ef wider than the region in which the normative data is defined. Therefore, the layer thickness distribution data generated in step S10 substantially includes the region in the fundus Ef that is to be compared with the normative data. This makes it possible to realize the point-to-point comparison (one-to-one comparison) between the layer thickness distribution data and the normative data.

(S12: Display Comparison Map)

The main controller 211 generates a comparison map representing the result of the comparison performed in step S11 and displays the comparison map on the display 241 (END).

<Actions and Effects>

Actions and effects of the ophthalmic apparatus according to the exemplary embodiment will be described.

An ophthalmic apparatus (1) according to an exemplary embodiment is capable of applying optical coherence tomography (OCT) to the fundus of a subject's eye, and includes an optical system, an optical scanner, an optical path length changing device, and a controller.

The optical system is configured to split light (L0) output from a light source (the light source unit 101) into measurement light (LS) and reference light (LR), project the measurement light onto the eye fundus, superpose returning light of the measurement light from the subject's eye on the reference light to generate interference light (LC), and detect the interference light.

The optical scanner (44) is configured to deflect the measurement light for scanning the eye fundus.

The optical path length changing device is configured to change at least one of the optical path length of the measurement light and the optical path length of the reference light. In the above exemplary embodiment, the combination of the retroreflector 41 and the retroreflector driver 41A corresponds to the optical path length changing device that changes the optical path length of the measurement light, and the combination of the retroreflector 114 and the retroreflector driver 114A corresponds to the optical path length changing device that changes the optical path length of the reference light.

The controller (the main controller 211, the scan size corrector 231) is configured to control the optical scanner (44) based on at least the optical path length of the measurement light and/or the optical path length of the reference light.

In the exemplary embodiment, the controller (the main controller 211, the scan size corrector 231) may be configured to control the deflection range (the maximum deflection angle) of the measurement light by the optical scanner (44), based on at least the optical path length of the measurement light and/or the optical path length of the reference light.

In the exemplary embodiment, the optical scanner (44) may be configured to be capable of deflecting the measurement light in a two dimensional manner. Further, the controller (the main controller 211, the scan size corrector 231) may be configured to control the two dimensional deflection range of the measurement light by the optical scanner (44), based on at least the optical path length of the measurement light and/or the optical path length of the reference light.

In the exemplary embodiment, the optical path length changing device (the combination of the retroreflector 114 and the retroreflector driver 114A) may be configured to change the optical path length of the reference light. Furthermore, the controller (the main controller 211, the scan size corrector 231) may be configured to apply the first deflection range when the optical path length of the reference light is equal to or greater than a predetermined threshold value, and apply the second deflection range larger than the first deflection range when the optical path length of the reference light is less than the predetermined threshold value. It may be also possible to prepare the relationship between optical path lengths and deflection that has three or more classes (three or more deflection ranges). In addition, information (e.g., graph) that represents continuous relationship between optical path lengths and deflection ranges may also be prepared.

In the exemplary embodiment, the optical path length changing device (the combination of the retroreflector 41 and the retroreflector driver 41A) may be configured to change the optical path length of the measurement light. Furthermore, the controller (the main controller 211, the scan size corrector 231) may be configured to apply the third deflection range when the optical path length of the measurement light is equal to or greater than a predetermined threshold value, and apply the fourth deflection range smaller than the third deflection range when the optical path length of the measurement light is less than the predetermined threshold value. It may be also possible to prepare the relationship between optical path lengths and deflection that has three or more classes (three or more deflection ranges). In addition, information (e.g., graph) that represents continuous relationship between optical path lengths and deflection ranges may also be prepared.

In the exemplary embodiment, the controller (the main controller 211, the scan size corrector 231) may be configured to calculate the deflection range (the maximum deflection angle) of the measurement light by the optical scanner (44) based on at least the optical path length of the measurement light and/or the optical path length of the reference light.

In the exemplary embodiment, the ophthalmic apparatus (1) may further include a focus adjustment device (the combination of the OCT focusing lens 43 and the OCT focus driver 43A) for performing focus adjustment of the optical system. Further, the controller (the main controller 211, the scan size corrector 231) may be configured to perform control of the optical scanner (44) based on at least the optical path length of the measurement light and the optical path length of the reference light, and a focus state of the optical system.

According to the exemplary embodiment including such the configuration described above, the area size of the eye fundus actually scanned can be corrected by controlling the optical scanner based on the condition of the optical system (e.g., the optical path length information, the focus information, etc.) regulated in accordance with the characteristics of the subject's eye (e.g., the axial length, the diopter, etc.), without having to refer to data acquired by another apparatus.

For example, the exemplary embodiment may be configured to control the optical scanner so as to acquire data of a region in the eye fundus whose size is substantially the same as that of the normative data prepared in advance (e.g., the size of 6 mm×6 mm). Alternatively, the exemplary embodiment may be configured to control the optical scanner so as to acquire data of a region in the eye fundus whose size is larger than that of the normative data.

Therefore, the present embodiment can be applied to screening examinations such as health check, unlike a conventional technique that requires data acquired by another apparatus to carry out the magnification correction. Further, the present embodiment can also be applied to examinations carried out at facilities that do not have an external device for acquiring the above data.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus capable of applying optical coherence tomography (OCT) to a fundus of a subject's eye, comprising:
    an optical system that splits light output from a light source into measurement light and reference light, projects the measurement light onto the fundus, generates interference light by superposing returning light of the measurement light from the subject's eye on the reference light, and detects the interference light;
    an optical scanner that deflects the measurement light for scanning the fundus;
    an optical path length changing device that changes at least one of an optical path length of the measurement light and an optical path length of the reference light;
    a controller that controls a deflection range of the measurement light by the optical scanner based on at least the optical path length;
    a data processor that constructs three dimensional image data from data acquired by scanning the fundus with the deflection range and generates layer thickness distribution data from the three dimensional image data; and
    a data comparator that performs comparison between the layer thickness distribution data and standard distribution data generated in advance.

2. The ophthalmic apparatus of claim 1, wherein
    the optical scanner is capable of deflecting the measurement light in a two dimensional manner, and
    the controller controls a two dimensional deflection range of the measurement light by the optical scanner based on at least the optical path length.

3. The ophthalmic apparatus of claim 1, wherein
    the optical path length changing device changes the optical path length of the reference light, and
    the controller applies a first deflection range when the optical path length of the reference light is equal to or greater than a predetermined threshold value, and applies a second deflection range larger than the first deflection range when the optical path length of the reference light is less than the predetermined threshold value.

4. The ophthalmic apparatus of claim 2, wherein
    the optical path length changing device changes the optical path length of the reference light, and
    the controller applies a first deflection range when the optical path length of the reference light is equal to or greater than a predetermined threshold value, and applies a second deflection range larger than the first deflection range when the optical path length of the reference light is less than the predetermined threshold value.

5. The ophthalmic apparatus of claim 1, wherein
    the optical path length changing device changes the optical path length of the measurement light, and
    the controller applies a third deflection range when the optical path length of the measurement light is equal to or greater than a predetermined threshold value, and applies a fourth deflection range smaller than the third deflection range when the optical path length of the measurement light is less than the predetermined threshold value.

6. The ophthalmic apparatus of claim 2, wherein
    the optical path length changing device changes the optical path length of the measurement light, and
    the controller applies a third deflection range when the optical path length of the measurement light is equal to or greater than a predetermined threshold value, and applies a fourth deflection range smaller than the third deflection range when the optical path length of the measurement light is less than the predetermined threshold value.

7. The ophthalmic apparatus of claim 1, wherein
    the controller calculates the deflection range based on at least the optical path length.

8. The ophthalmic apparatus of claim 2, wherein
    the controller calculates the deflection range based on at least the optical path length.

9. The ophthalmic apparatus of claim 1, further comprising a focus adjustment device for performing focus adjustment of the optical system,
    wherein the controller performs control of the optical scanner based on the optical path length and a focus state of the optical system.

10. The ophthalmic apparatus of claim 2, further comprising a focus adjustment device for performing focus adjustment of the optical system,
    wherein the controller performs control of the optical scanner based on the optical path length and a focus state of the optical system.

11. The ophthalmic apparatus of claim 3, further comprising a focus adjustment device for performing focus adjustment of the optical system,
    wherein the controller performs control of the optical scanner based on the optical path length and a focus state of the optical system.

12. The ophthalmic apparatus of claim 4, further comprising a focus adjustment device for performing focus adjustment of the optical system,
    wherein the controller performs control of the optical scanner based on the optical path length and a focus state of the optical system.

13. The ophthalmic apparatus of claim 5, further comprising a focus adjustment device for performing focus adjustment of the optical system,
    wherein the controller performs control of the optical scanner based on the optical path length and a focus state of the optical system.

14. The ophthalmic apparatus of claim 6, further comprising a focus adjustment device for performing focus adjustment of the optical system,
    wherein the controller performs control of the optical scanner based on the optical path length and a focus state of the optical system.

15. The ophthalmic apparatus of claim 7, further comprising a focus adjustment device for performing focus adjustment of the optical system,
    wherein the controller performs control of the optical scanner based on the optical path length and a focus state of the optical system.

16. The ophthalmic apparatus of claim 8, further comprising a focus adjustment device for performing focus adjustment of the optical system,
    wherein the controller performs control of the optical scanner based on the optical path length and a focus state of the optical system.

17. The ophthalmic apparatus of claim 1, further comprising a display controller that displays a comparison map representing a result of the comparison performed by the data comparator on a display.

* * * * *